United States Patent
Zhang et al.

(10) Patent No.: US 8,855,755 B2
(45) Date of Patent: Oct. 7, 2014

(54) DISTINGUISHING BETWEEN TREATABLE AND NON-TREATABLE HEART RHYTHMS

(75) Inventors: Xusheng Zhang, Shoreview, MN (US);
Robert W. Stadler, Shoreview, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 1323 days.

(21) Appl. No.: 12/430,301

(22) Filed: Apr. 27, 2009

(65) Prior Publication Data
US 2010/0274148 A1    Oct. 28, 2010

(51) Int. Cl.
| | |
|---|---|
| A61B 5/0468 | (2006.01) |
| A61N 1/365 | (2006.01) |
| A61N 1/362 | (2006.01) |
| A61B 5/0464 | (2006.01) |
| A61B 5/046 | (2006.01) |
| A61B 5/00 | (2006.01) |
| A61N 1/39 | (2006.01) |
| A61B 5/0452 | (2006.01) |

(52) U.S. Cl.
CPC .......... *A61N 1/3621* (2013.01); *A61N 1/36507* (2013.01); *A61B 5/726* (2013.01); *A61N 1/3962* (2013.01); *A61B 5/7264* (2013.01); *A61B 5/0464* (2013.01); *A61B 5/04525* (2013.01); *A61B 5/046* (2013.01)
USPC ............................ 600/516; 600/515; 600/519

(58) Field of Classification Search
USPC ...................................... 600/513–521; 607/14
See application file for complete search history.

(56) References Cited

U.S. PATENT DOCUMENTS

| | | |
|---|---|---|
| 5,000,189 A | 3/1991 | Throne et al. |
| 5,086,772 A | 2/1992 | Larnard et al. |
| 5,280,792 A | 1/1994 | Leong et al. |
| 5,330,508 A | 7/1994 | Gunderson |
| 5,379,776 A | 1/1995 | Murphy et al. |
| 5,423,863 A | 6/1995 | Felblinger et al. |

(Continued)

FOREIGN PATENT DOCUMENTS

| | | |
|---|---|---|
| EP | 0360412 A1 | 3/1990 |
| EP | 1219237 A2 | 7/2002 |

(Continued)

OTHER PUBLICATIONS (PCT/US2010/030711) PCT Notification of Transmittal of the International Search Report and the Written Opinion of the International Searching Authority, Jun. 24, 2010, 10 pages.

*Primary Examiner* — Christopher D Koharski
*Assistant Examiner* — Michael Carey
(74) *Attorney, Agent, or Firm* — Michael J. Ostrom; Stephen W. Bauer

(57) ABSTRACT

Techniques are described for distinguishing between treatable and non-treatable heart rhythms. A medical device that operates in accordance with the techniques analyzes characteristics over several cardiac event intervals to detect initiation of a sudden rate onset. After detection of the initiation of the sudden rate onset, the IMD analyzes a morphology of an EGM associated with a selected cardiac event within the first several beats after the initiation of sudden rate onset. In one example, the IMD analyzes the morphology of the EGM associated with the first cardiac event immediately subsequent to the initiation of the sudden rate onset. If the morphology of the EGM of the selected cardiac event is abnormal compared to template EGM, the rhythm is classified as treatable. Otherwise, the rhythm is classified as non-treatable.

25 Claims, 10 Drawing Sheets

(56) References Cited

U.S. PATENT DOCUMENTS

| | | | |
|---|---|---|---|
| 5,873,897 A | 2/1999 | Armstrong et al. | |
| 6,427,083 B1 | 7/2002 | Owen et al. | |
| 6,978,177 B1 | 12/2005 | Chen et al. | |
| 6,980,860 B2 * | 12/2005 | Stadler et al. | 607/14 |
| 7,076,290 B2 | 7/2006 | Sheth et al. | |
| 7,474,916 B2 | 1/2009 | Gutierrez | |
| 2003/0144700 A1 | 7/2003 | Brown et al. | |
| 2004/0254613 A1 | 12/2004 | Ostroff et al. | |
| 2006/0025822 A1 | 2/2006 | Zhang | |
| 2006/0155201 A1 | 7/2006 | Schwartz et al. | |
| 2006/0217621 A1 | 9/2006 | Kim et al. | |
| 2006/0247703 A1 | 11/2006 | Gutierrez | |
| 2006/0281998 A1 | 12/2006 | Li | |
| 2007/0191894 A1 | 8/2007 | Li | |
| 2007/0232948 A1 | 10/2007 | Stadler et al. | |
| 2007/0239051 A1 | 10/2007 | Ghanem et al. | |
| 2007/0239220 A1 | 10/2007 | Greenhut et al. | |
| 2007/0270704 A1 | 11/2007 | Ghanem et al. | |
| 2007/0276276 A1 | 11/2007 | Cao et al. | |
| 2008/0177194 A1 | 7/2008 | Zhang et al. | |
| 2008/0269624 A1 | 10/2008 | Zhang et al. | |
| 2008/0269813 A1 | 10/2008 | Greenhut et al. | |
| 2008/0288009 A1 | 11/2008 | Kim et al. | |

FOREIGN PATENT DOCUMENTS

| | | |
|---|---|---|
| WO | 03003905 | 1/2003 |
| WO | 2005112749 | 12/2005 |
| WO | 2008137529 | 11/2008 |

* cited by examiner

DISTINGUISHING BETWEEN TREATABLE AND NON-TREATABLE HEART RHYTHMS

TECHNICAL FIELD

This disclosure relates to implantable medical devices (IMDs), and, more particularly, to distinguishing between treatable and non-treatable heart rhythms of a patient.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. IMDs may deliver therapy to or monitor conditions of a variety of organs, nerves, muscle or tissue, such as the heart, brain, stomach, spinal cord, pelvic floor, or the like. Implantable medical leads may be configured to allow electrodes or other sensors to be positioned at desired locations for delivery of electrical stimulation or sensing of physiological conditions. For example, electrodes or sensors may be carried at a distal portion of a lead. A proximal portion of the lead may be coupled to an implantable medical device housing, which may contain circuitry such as signal generation circuitry and/or sensing circuitry.

Some IMDs, such as cardiac pacemakers or implantable cardioverter-defibrillators (ICDs), provide therapeutic electrical stimulation to or monitor the heart of the patient via electrodes carried by one or more implantable leads. The leads are typically implanted transvenous, i.e., implanted in the heart through one or more veins, sometimes referred to as endocardial leads. Other IMDs, sometimes referred to as subcutaneous devices, may include leads that are not implanted within the heart. Instead, these leads are implanted outside of the heart and may be referred to as epicardial leads. In either case, the electrical stimulation provided by the IMD may include signals such as pacing pulses, cardiac resynchronization pulses, cardioversion shocks or defibrillation shocks to address abnormal cardiac rhythms such as bradycardia, tachycardia or fibrillation.

In some cases, the IMD senses signals representative of intrinsic depolarizations of the heart and analyzes the sensed signals to identify normal or abnormal rhythms. Upon detection of an abnormal rhythm, the device may deliver an appropriate electrical stimulation signal or signals to restore or maintain a more normal rhythm. For example, in some cases, an IMD may deliver pacing pulses to the heart upon detecting tachycardia or bradycardia, and deliver cardioversion or defibrillation shocks to the heart upon detecting tachycardia or fibrillation.

SUMMARY

In general, the disclosure is directed to techniques for discriminating between treatable, e.g., ventricular tachycardia (VT) or ventricular fibrillation (VF), and non-treatable heart rhythms, e.g., supra-ventricular tachycardia (SVT), of a heart of a patient. An implantable medical device (IMD) operating in accordance with the techniques analyzes characteristics over several cardiac event intervals to detect initiation of sudden rate onset. Sudden rate onset occurs when the heart rate of the patient rapidly increases in a very short period of time, e.g., over a relatively few beats (4 or 5 beats, for instance). In one example, the IMD may analyze the variation over the most recent cardiac event intervals and the relative change of the most recent cardiac event intervals compared to previous cardiac event intervals to detect initiation of sudden rate onset. In particular, the IMD may detect initiation of sudden rate onset when the variation is less than a variation threshold and the relative change is greater than a relative change threshold.

To reduce the likelihood of misclassification of the rhythm, the IMD analyzes a morphology of an EGM associated with a selected cardiac event within the first several beats after the initiation of sudden rate onset. In one example, the IMD analyzes the morphology of the EGM associated with the first cardiac event immediately subsequent to the initiation of the sudden rate onset. The IMD analyzes the change of one or more beat morphology parameters of the EGM as compared to corresponding beat morphology parameters of a template EGM to determine whether the selected cardiac event is abnormal compared to the cardiac event corresponding to the template EGM. If the selected cardiac event is abnormal the rhythm is classified as treatable. Otherwise, the rhythm is classified as non-treatable.

In one example, the disclosure provides a method comprising detecting initiation of rate onset of a rhythm of a heart of a patient, obtaining an electrogram (EGM) associated with a cardiac event after a location of the initiation of the rate onset, analyzing a morphology of the EGM associated with the cardiac event after the location of the initiation of the rate onset, and determining whether the rhythm is indicative of a treatable rhythm based on the analysis of the morphology of the EGM.

In another example, the disclosure provides an implantable medical device (IMD) comprising a sensing module configured to acquire signals associated with cardiac events of a heart of a patient via at least one sensor and a processor configured to detect initiation of rate onset of a rhythm of the heart based on the acquired signals, obtain an electrogram (EGM) associated with one of the cardiac events after a location of the initiation of the rate onset, analyze a morphology of the EGM associated with the cardiac event after the location of the initiation of the rate onset, and determine whether the rhythm is indicative of a treatable rhythm based on the analysis of the morphology of the EGM.

In another example, the disclosure provides a computer-readable storage medium comprising instructions that, when executed by a processor in an implantable medical device, cause the processor to detect initiation of rate onset of a rhythm of a heart of a patient, obtain an electrogram (EGM) associated with a cardiac event after a location of the initiation of the rate onset, analyze a morphology of the EGM associated with the cardiac event after the location of the initiation of the rate onset, and determine whether the rhythm is indicative of a treatable rhythm based on the analysis of the morphology of the EGM.

In a further example, the disclosure provides a medical device that includes means for detecting initiation of rate onset of a rhythm of a heart of a patient, means for obtaining an electrogram (EGM) associated with a cardiac event after a location of the initiation of the rate onset, means for analyzing a morphology of the EGM associated with the cardiac event after the location of the initiation of the rate onset, and means for determining whether the rhythm is indicative of a treatable rhythm based on the analysis of the morphology of the EGM.

This summary is intended to provide an overview of the subject matter described in this disclosure. It is not intended to provide an exclusive or exhaustive explanation of the invention as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

In general, this disclosure describes techniques for distinguishing between treatable arrhythmias and non-treatable arrhythmias. Treatable arrhythmias refer to abnormal heart rhythms for which stimulation therapy is delivered to one or both of the ventricles. Treatable arrhythmias may include ventricular tachycardia (VT) or ventricular fibrillation (VF). Treatable arrhythmias generally pose an immediate danger to the patient and therapy is needed in order to ensure the safety of the patient. Non-treatable arrhythmias, on the other hand, refer to abnormal heart rhythms that typically do not require stimulation therapy to be delivered to either of the ventricles. Non-treatable arrhythmias may include supra-ventricular tachycardia (SVT), which includes sinus tachycardia, atrial tachycardia (AT), atrial fibrillation (AF), atrial flutter, atrioventricular nodal reentrant tachycardia (AVNRT), atrioventricular reciprocating tachycardia (AVRT), or the like. Non-treatable arrhythmias do not generally pose an immediate danger to the patient. As such, non-treatable arrhythmias may go untreated, i.e., no stimulation therapy is delivered to the heart. In other instances, non-treatable arrhythmias may be treated using stimulation therapy, but the stimulation therapy is not delivered to the ventricles of the patient.

Accurately determining whether the heart rhythm is treatable or non-treatable prevents inadvertent delivery of therapy to a ventricle of the patient when no therapy to the ventricle is necessary (e.g., in the case of a rhythm mischaracterized as a treatable arrhythmia) or withholding stimulation therapy when the therapy to the ventricle is necessary (e.g., in the case of a rhythm mischaracterized as a non-treatable arrhythmia). Unnecessary delivery of stimulation therapy to the patient may be uncomfortable for the patient, needlessly depletes the power source of the medical device and, in some patients or circumstances, can induce more dangerous arrhythmias.

Figure 1:
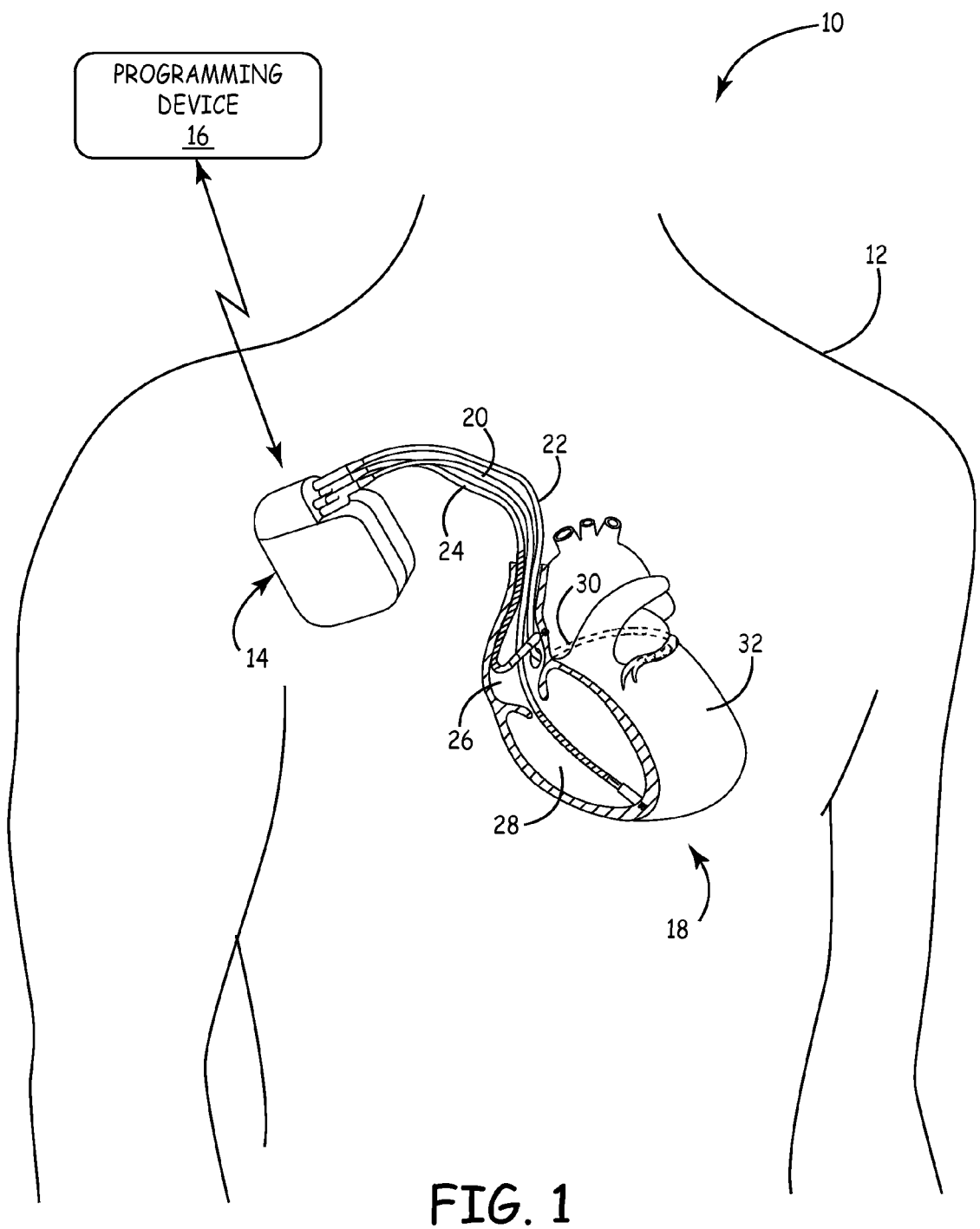
FIG. 1 is a conceptual diagram illustrating an example therapy system that may be used to provide therapy to patient.

FIG. 1 is a conceptual diagram illustrating an example therapy system 10 that may be used to provide therapy to patient 12. Therapy system 10 includes an IMD 14 and leads 20, 22 and 24 that extend from IMD 14. Therapy system 10 may also include a programming device 16 that wirelessly communicates with IMD 14.

In the example illustrated in FIG. 1, IMD 14 is an implantable cardiac device that provides electrical stimulation therapy to a heart 18 of patient 12. The electrical stimulation therapy to heart 18, sometimes referred to as cardiac rhythm management therapy, may include pacing, cardioversion, defibrillation and/or cardiac resynchronization therapy (CRT). As such, IMD 14 may operate as an implantable pacemaker, cardioverter, and/or defibrillator. The electrical stimulation therapy provided by IMD 14 depends on the arrhythmia detected by IMD 14, as described in further detail below.

IMD 14 delivers the electrical stimulation therapy to heart 18 via one or more electrodes located on leads 20, 22 and/or 24 and implanted within or adjacent to one or more atria or ventricles of heart 18. In the example illustrated in FIG. 1, leads 20, 22 and 24 are coupled to IMD 14 and extend into heart 18 of patient 12. In the example shown in FIG. 1, right ventricular (RV) lead 20 extends through one or more veins (not shown), the superior vena cava (not shown), and right atrium 26, and into right ventricle 28 of heart 18. Left ventricular (LV) coronary sinus lead 22 extends through one or more veins, the vena cava, right atrium 26, and into the coronary sinus 30 to a region adjacent to the free wall of left ventricle 32 of heart 18. Right atrial (RA) lead 24 extends through one or more veins and the vena cava, and into the right atrium 26 of heart 18. In other examples, IMD 14 may deliver stimulation therapy to heart 18 by delivering stimulation to an extravascular tissue site in addition to or instead of delivering stimulation via electrodes of intravascular leads 20, 22 and 24.

In addition to delivering therapy to heart 18, electrodes of leads 20, 22 and 24 may sense electrical signals attendant to depolarization and repolarization of heart 18 (e.g., cardiac signals or events). IMD 14 may analyze the sensed cardiac signals or events to monitor a rhythm of heart 18 to detect an arrhythmia. As described above, the electrical stimulation therapy provided by IMD 14 may depend on the type of arrhythmia detected by IMD 14. For example, IMD 14 may provide stimulation therapy (e.g., anti-tachycardia pacing (ATP), defibrillation shock and/or cardioversion shock) to ventricle 28 of patient 12 in response to detecting that the rhythm is a treatable arrhythmia, such as VT or VF. As another example, IMD 14 may withhold delivery of stimulation therapy to ventricle 28 in response to detecting that the rhythm is a non-treatable arrhythmia, such as SVT. Instead, IMD 14 may deliver no therapy or provide therapy to atrium 26 to treat the SVT.

In some instances, SVT may be conducted to ventricles 28 and/or 32 and falsely detected as VT or VF. This results in IMD 14 delivering ventricular stimulation therapy (e.g., ATP, cardioversion or defibrillation) when no ventricular therapy is needed. Unnecessary delivery of electrical stimulation therapy to ventricles 28 and/or 32 may be uncomfortable for patient 12 and, in some patients, may induce dangerous arrhythmias. Additionally, delivery of unnecessary electrical stimulation therapy needlessly depletes the power source of IMD 14. It is desirable, therefore, to avoid delivering a therapy to ventricles 28 and/or 32 due to inappropriate arrhythmia detection.

The techniques of this disclosure may increase the accuracy with which IMD 14 detects arrhythmias and discriminates between treatable and non-treatable arrhythmias. As will be described in further detail below, IMD 14 combines cardiac event interval analysis and EGM morphology analysis together to determine whether an abnormal rhythm is a treatable or non-treatable arrhythmia. In operation, IMD 14 determines cardiac event intervals that correspond to the amount of time between cardiac events, such as between two sensed ventricular depolarizations, two sensed atrial depolarizations, between one sensed ventricular event and one sensed atrial event, or a combination thereof.

IMD 14 may analyze characteristics over several cardiac event intervals to detect sudden rate onset. Sudden rate onset occurs when the heart rate of patient 12 rapidly increases in a very short period of time, e.g., over a relatively few beats (4 or 5 beats, for instance). IMD may analyze relative changes and/or variations over the last N cardiac event intervals. In one example, N is equal to nine and the cardiac event intervals are R-R intervals corresponding to amount of time between successive R-waves. IMD 14 may determine a relative change between an average (e.g., mean, median or mode) of the last four R-R intervals of the nine R-R intervals and an average of the first four R-R intervals of the nine R-R intervals. IMD 14 may also determine a variability of the last four R-R intervals of the nine R-R intervals. IMD 14 may detect sudden rate onset when the determined variability is less than a variability threshold value and the determined difference is greater than a relative change threshold value.

Although in the example described above sudden rate onset detection is described in the context of nine R-R intervals, IMD 14 may analyze more or fewer cardiac event intervals in making the sudden rate onset determination. Additionally, IMD 14 may use intervals between other cardiac events, such as P-P intervals corresponding to the amount of time between successive P-waves, or a combination of different types of cardiac intervals.

Some arrhythmias cause detection challenges for detection schemes that analyze cardiac event intervals. For example, certain types of SVTs produce ventricular rates in the VT/VF detection zones and thus result in a sudden rate onset similar to that of VT or VF. As such, IMD 14 may inadvertently detect the SVT as VT or VF resulting in delivery of a ventricular therapy. In treatable arrhythmias, such as VT or VF, a change in beat morphology may accompany the sudden rate onset, particularly within the first few (4-6) beats after the sudden rate onset. As such, the first few beats during VT or VF initiation have morphologies that demonstrate dramatic difference when compared with the morphology of a beat during normal sinus rhythm. Additionally, the morphologies of the first few beats may vary significantly among one another. However, the sequential beats after the VT initiation may gradually stabilize.

To reduce the likelihood of such a false detection, the techniques of this disclosure analyze an EGM morphology of a beat within the first few beats after the sudden rate onset initiation to distinguish between treatable and non-treatable arrhythmias. For example, IMD 14 may determine whether the rhythm is indicative of a treatable rhythm by analyzing a morphology of the EGM associated with a beat located immediately adjacent to a location at which the sudden rate onset is determined to occur. In other words, IMD 14 may analyze the morphology of the EGM associated with the first beat after the sudden rate onset initiation. The beat located in the position immediately after the sudden rate onset initiation is referred to herein as the "onset initiation beat." In the example described above in which nine R-R intervals are analyzed, the onset initiation beat is the sixth beat of the ten beats used to determine the nine R-R intervals. Other ones of the first few beats after onset initiation may be analyzed, such as a second, third, fourth, fifth or sixth beat. However, analyzing beats closer to the onset initiation may provide slightly better results since the successive beats begin to stabilize.

If IMD 14 determines the EGM of the onset initiation beat or other analyzed beat is abnormal compared to a template EGM, IMD 14 classifies the arrhythmia as treatable. The template EGM may be an EGM during a known normal sinus rhythm or a known abnormal sinus rhythm. Alternatively, the template EGM may be an EGM of a beat located just prior to rate onset initiation or one of the beats located after the rate onset initiation as both of these EGMs may differ from the EGM of a beat of a treatable rhythm. If IMD 14 determines the EGM of the onset initiation beat or other analyzed beat is abnormal compared to the template EGM, IMD 14 classifies the arrhythmia as treatable. IMD 14 provides a therapy in accordance with the therapy program associated with the detected arrhythmia.

A user, such as a physician, technician, or other clinician, may interact with programming device 16 to communicate with IMD 14. For example, the user may interact with programming device 16 to retrieve physiological or diagnostic information from IMD 14. For example, the user may use programming device 16 to retrieve information from IMD 14 regarding the rhythm of the heart of patient 12, trends therein over time, or cardiac arrhythmia episodes. As another example, the user may use programming device 16 to retrieve information from IMD 14 regarding other sensed physiological parameters of patient 12, such as electrical depolarization/repolarization signals from the heart (referred to as "electrogram" or EGM), intracardiac or intravascular pressure, activity, posture, respiration or thoracic impedance. As another example, the user may use programming device 16 to retrieve information from IMD 14 regarding the performance or integrity of IMD 14 or other components of therapy system 10, such as leads or a power source of IMD 14.

The user may also interact with programming device 16 to program IMD 14, e.g., select values for operational parameters of IMD 14. For electrical stimulation therapies, for example, the user may interact with programming device 16 to program one or more sets of therapy parameters, select therapy programs or progressions of therapy programs to be used during particular arrhythmias, select an electrode or combination of electrodes of leads 20, 22 and 24 to use for delivering electrical stimulation (pulses or shocks), select parameters for the electrical pulse or shock (e.g., pulse amplitude, pulse width, or pulse rate), select electrodes or sensors for use in detecting a physiological parameter of patient 12, or the like. By programming these parameters, the physician or other user can attempt to generate an efficacious therapy for patient 12 that is delivered via the selected electrodes.

Programming device 16 may be a dedicated hardware device with dedicated software for programming of IMD 14. Alternatively, programming device 16 may be an off-the-shelf computing device running an application that enables programming device 16 to program IMD 14. In some examples, programming device 16 may be a handheld computing device or a computer workstation. Programming device 16 may, in some instances, include a programming head that may be placed proximate to the patient's body near the implant site of IMD 14 in order to improve the quality or security of communication between IMD 14 and programming device 16. Programming device 16 may include a user interface that receives input from the user and/or displays data to the user.

Programming device 16 may communicate with IMD 14 via wireless communication using any techniques known in the art. Examples of communication techniques may include, for example, magnetic telemetry, low frequency telemetry or radiofrequency (RF) telemetry, but other techniques are also contemplated. In some instances, programming device 16 and IMD 14 may communicate in the 402-405 MHz frequency band in accordance with the Medical Implant Communications Service (MICS) protocol.

Figure 2:
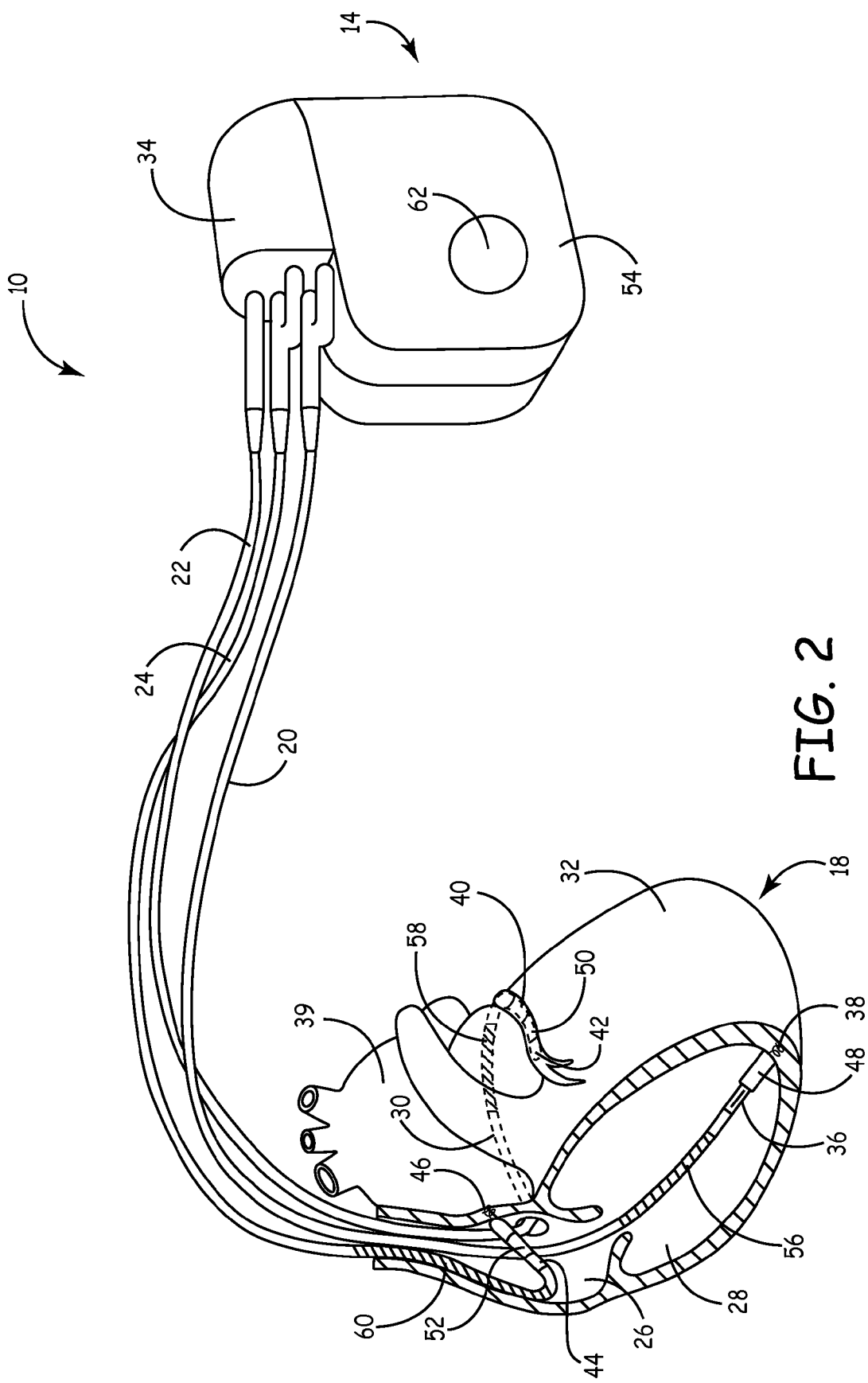
FIG. 2 is a conceptual diagram illustrating the IMD and leads of the therapy system of FIG. 1 in greater detail.

FIG. 2 is a conceptual diagram illustrating IMD 14 and leads 20, 22 and 24 of therapy system 10 in greater detail. Leads 20, 22 and 24 are electrically coupled to a stimulation module, a sensing module, or other modules of IMD 14 via connector block 34. In some examples, proximal ends of leads 20, 22 and 24 include electrical contacts that electrically couple to respective electrical contacts within connector block 34. In addition, in some examples, leads 20, 22 and 24 are mechanically coupled to connector block 34 with the aid of set screws, connection pins or another suitable mechanical coupling mechanism.

Each of the leads 20, 22 and 24 includes an elongated insulative lead body, which may carry a number of concentric coiled conductors separated from one another by tubular insulative sheaths. Other lead configurations are also contemplated, such as lead configurations that do not include coiled conductors, but instead a different type of conductor. In the illustrated example, bipolar electrodes 36 and 38 are located proximate to a distal end of lead 20. In addition, bipolar electrodes 40 and 42 are located proximate to a distal end of lead 22 and bipolar electrodes 44 and 46 are located proximate to a distal end of lead 24.

Electrodes 36, 40, and 44 may take the form of ring electrodes, and electrodes 38, 42, and 46 may take the form of extendable helix tip electrodes mounted retractably within insulative electrode heads 48, 50, and 52, respectively. Each of the electrodes 36, 38, 40, 42, 44, and 46 is electrically coupled to a respective one of the conductors within the lead body of its associated lead 20, 22 and 24, and thereby coupled to respective ones of the electrical contacts on the proximal end of leads 20, 22 and 24. In other embodiments, electrodes 36, 38, 40, 42, 44, and 46 may be other types of electrodes.

Electrodes 36, 38, 40, 42, 44, and 46 may sense electrical signals attendant to the depolarization and repolarization of heart 18. The electrical signals are conducted to IMD 14 via the one or more conductors of respective leads 20, 22 and 24. In some examples, IMD 14 also delivers pacing pulses via electrodes 36, 38, 40, 42, 44, and 46 to cause depolarization of cardiac tissue of heart 14. In some examples, as illustrated in FIG. 2, IMD 14 includes one or more housing electrodes, such as housing electrode 62, which may be formed integrally with an outer surface of hermetically-sealed housing 54 of IMD 14 or otherwise coupled to housing 54. In some examples, housing electrode 62 is defined by an uninsulated portion of an outward facing portion of housing 54 of IMD 14. In some examples, housing electrode 62 comprises substantially all of housing 54. Divisions between insulated and uninsulated portions of housing 54 may be employed to define two or more housing electrodes. Any of the electrodes 36, 38, 40, 42, 44, and 46 may be used for unipolar sensing or pacing in combination with housing electrode 62. As such, the configurations of electrodes used by IMD 14 for sensing and pacing may be unipolar or bipolar depending on the application.

Leads 20, 22 and 24 also include elongated electrodes 56, 58, and 60, respectively, which may, in some instances, take the form of a coil. IMD 14 may deliver high energy electrical shocks, e.g., defibrillation or cardioversion shocks, to heart 18 via any combination of elongated electrodes 56, 58, and 60, and housing electrode 62. In particular, IMD 14 may deliver the high energy electrical shocks in response to determining that a detected arrhythmia is treatable. Electrodes 36, 38, 40, 42, 44, 46, 56, 58, 60, and 62 may be fabricated from any suitable electrically conductive material, including, but not limited to, platinum, platinum alloy or other materials known to be usable in implantable defibrillation electrodes.

The configuration of therapy system 10 illustrated in FIGS. 1 and 2 are merely examples. In other examples, therapy system 10 may include more or fewer leads extending from IMD 14. For example, IMD 14 may be coupled to two leads, e.g., one lead implanted within right atrium 26 and the other implanted within right ventricle 28. In another example, IMD 14 may be coupled to a single lead that is implanted within either an atrium or ventricle of heart 18. As a further example, the therapy system may include three transvenous leads located as illustrated in FIGS. 1 and 2, and an additional lead located within or proximate to left atrium 32. As such, IMD 14 may be used for single chamber or multi-chamber cardiac rhythm management therapy. In addition to more or fewer leads, each of leads 20, 22 and 24 may include more or fewer electrodes.

In still other examples, a therapy system may include epicardial leads and/or patch electrodes instead of or in addition to the transvenous leads 20, 22 and 24 illustrated in FIGS. 1 and 2. In other words, IMD 14 may be a subcutaneous cardiac device. Further, IMD 14 need not be implanted within patient 12. In examples in which IMD 14 is not implanted in patient 12, IMD 14 may deliver defibrillation pulses and other therapies to heart 18 via percutaneous leads that extend through the skin of patient 12 to a variety of positions within or outside of heart 18.

Figure 3:
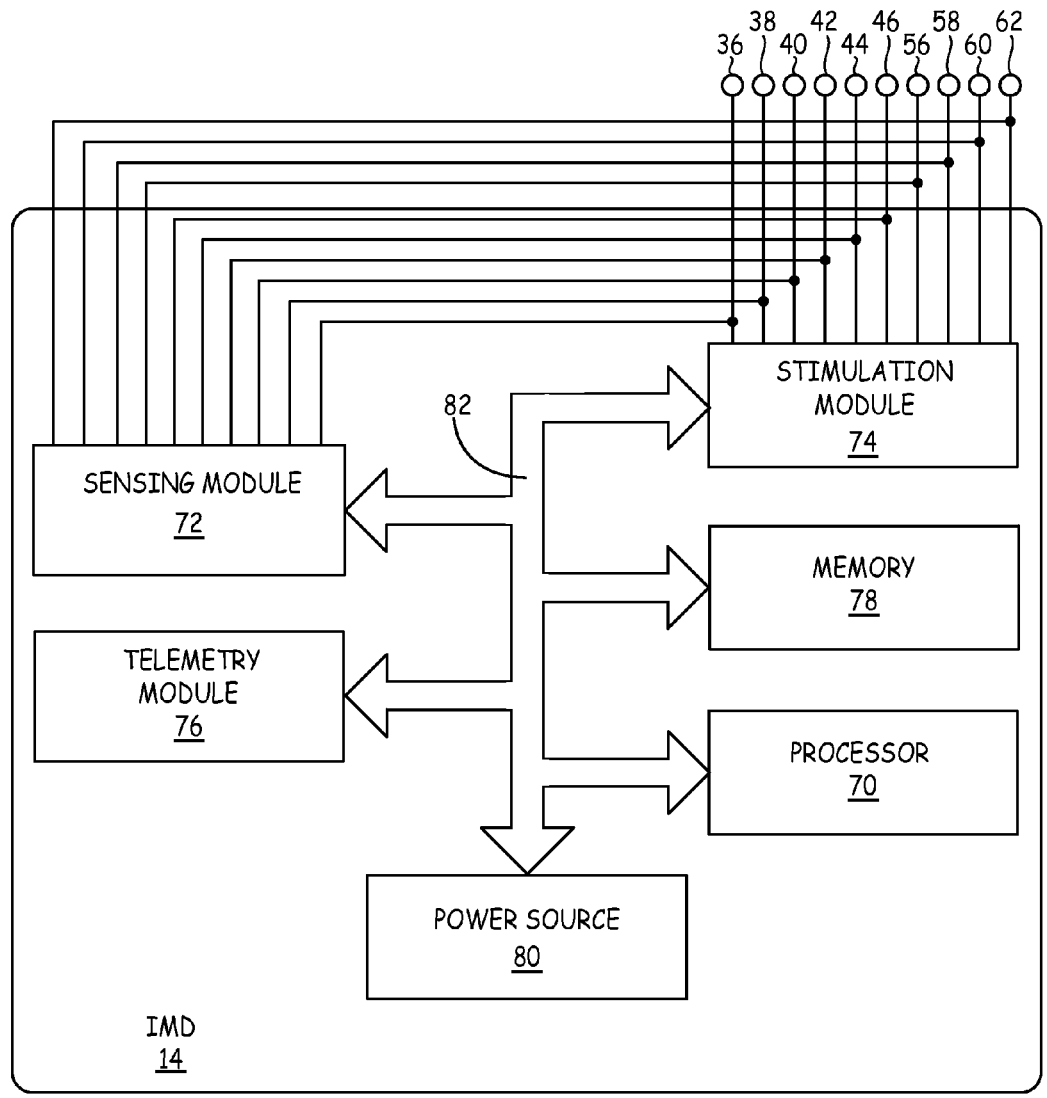
FIG. 3 is a functional block diagram of an example configuration of components of an IMD.

FIG. 3 is a functional block diagram of an example configuration of components of IMD 14. In the example illustrated by FIG. 3, IMD 14 includes a processor 70, sensing module 72, stimulation module 74, telemetry module 76, memory 78, and power source 80. The various components of IMD 14 are interconnected by a data bus 82. In other examples, the various components of IMD 14 may be interconnected by a number of point-to-point connections or a combination of one or more data buses and one or more point-to-point connections.

Processor 70 may include one or more of a microprocessor, a controller, a digital signal processor (DSP), an application specific integrated circuit (ASIC), a field-programmable gate array (FPGA), or equivalent discrete or integrated circuitry, including analog circuitry, digital circuitry, or logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof.

Memory 78 may include computer-readable instructions that, when executed by processor 70, cause components of IMD 14 to perform various functions attributed to the respective components in this disclosure. Memory 78 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The various components of IMD 14 are coupled to power source 80, which may include a non-rechargeable battery, rechargeable storage device such as a rechargeable battery or capacitor (which may be recharged internally or transcutaneously with the use of electromagnetic or piezoelectric transformers), energy-harvesting device, or a combination thereof. A non-rechargeable battery may be capable of holding a charge for several years, while a rechargeable battery may be inductively charged from an external device, e.g., on a daily or weekly basis. Power source 80 also may include power supply circuitry (not shown in FIG. 3) for providing regulated voltage and/or current levels to power the components of IMD 14.

Processor 70 controls electrical stimulation module 74 to deliver stimulation therapy to heart 18. Processor 70 may control electrical stimulation module 74 to deliver stimulation according to a selected one or more therapy programs, which may be stored in memory 78. For example, processor 70 may control electrical stimulation module 74 to deliver electrical pacing pulses, cardiac resynchronization pulses, or cardioversion or defibrillation shocks with the amplitudes, pulse widths, frequencies, and/or electrode polarities specified by the selected therapy programs. The type of therapy program provided may, for example, be dependent on the type of arrhythmia detected, whether a previous therapy program was effective, or the like.

Electrical stimulation module 74 is electrically coupled to electrodes 36, 38, 40, 42, 44, 46, 56, 58, 60, and 62, e.g., via conductors of the respective lead 20, 22 and 24, or, in the case of housing electrode 62, via an electrical conductor disposed within housing 54 of IMD 14. Electrical stimulation module 74 may include a switch module (not shown in FIG. 3) and processor 70 may use the switch module to select, e.g., via a data/address bus 82, which of the available electrodes to us to deliver pacing, resynchronization, cardioversion, or defibrillation pulses/shocks. The switch module may include a switch array, switch matrix, multiplexer, or any other type of switching device suitable to selectively couple stimulation energy to selected electrodes.

Sensing module 72 is configured to receive signals sensed by one or more sensors connected to sensing module 72. The signal sensed by the one or more sensors may include cardiac events, such as electrical signals attendant to depolarization and repolarization of heart 18. Sensing module 72 is electrically coupled to electrodes 36, 38, 40, 42, 44, 46, 56, 58, 60, and 62, e.g., via conductors of the respective lead 20, 22 and 24, or, in the case of housing electrode 62, via an electrical conductor disposed within housing 54 of IMD 14. In this case, electrodes 36, 38, 40, 42, 44, 46, 56, 58, 60, and 62 are the sensors connected to sensing module 72. Sensing module 72 may include a switch module and processor 80 may use the switch module to select, e.g., via a data/address bus 82, which of the available electrodes are used to sense electrical cardiac signals of heart 18. In this manner, sensing module 72 is capable of monitoring signals from a variety of electrode sensing vectors formed by different combinations of electrodes 36, 38, 40, 42, 44, 46, 56, 58, 60, and 62. The switch module may include a switch array, switch matrix, multiplexer, or any other type of switching device suitable to selectively couple the selected electrodes to the sensing circuitry of sensing module 72. In some instances, sensing module 72 and stimulation module 74 may share a switch module.

Sensing module 72 may receive signals sensed by various other sensors instead of, or in addition to, the signals sensed by the combinations of electrodes 36, 38, 40, 42, 44, 46, 56, 58, 60 and 62. For example, sensing module 72 may receive signals from one or more sensors that sense intravascular pressure, blood pressure, blood flow, acceleration, displacement, motion, respiration, or blood/tissue chemistry such as oxygen saturation, carbon dioxide, pH, protein levels, enzyme levels or other physiological parameter. Sensing module 72 may couple to these various other sensors via a wired connection or a wireless connection, e.g., using telemetry module 76.

Sensing module 72 may store the sensed signals in memory 78. In some instances, sensing module 72 may store the sensed signals in raw form. In other instances, sensing module 72 may process the sensed signals and store the processed signals in memory 78. For example, sensing module 72 may amplify and filter the sensed signal and store the filtered signal in memory 78. The signals stored by sensing module 72 may, in some cases, be retrieved and further processed by processor 70. Additionally, processor 70 may control telemetry module 76 to send the signals stored by sensing module 72 to another device, such as programming device 16 (FIG. 1) or another implanted or external device.

Under the control of processor 70, telemetry module 76 may receive data from and send data to programming device 16 (or other external or implanted device) with the aid of an antenna, which may be internal and/or external to IMD 14. Telemetry module 76 includes any suitable hardware, firmware, software or any combination thereof for communicating with another device. For example, telemetry module 76 may include appropriate modulation, demodulation, frequency conversion, filtering, and amplifier components for transmission and reception of data.

As described above, the type of therapy program provided by stimulation module 74 may be dependent on the type of heart rhythm detected, e.g., whether it is treatable (e.g., VT/VF) or non-treatable (e.g., SVT). Processor 70 controls stimulation module 74 to deliver electrical stimulation therapy to at least one ventricle of patient 12 in response to detecting the rhythm is treatable. For example, processor 70 may control stimulation module 74 to deliver a cardioversion shock in response to detecting VT or control stimulation module 74 to deliver a defibrillation shock in response to detecting VF. As another example, processor 70 may control stimulation module 74 to deliver ATP to at least one ventricle of patient 12 in response to detecting the rhythm as treatable. In other examples, processor 70 may control stimulation module 74 to deliver a progression of therapies, e.g., shocks with increasing energy levels or various anti-tachycardia pacing regimens followed by shocks in response to detecting the rhythm as treatable.

Rhythms detected to be non-treatable, on the other hand, do not require stimulation therapy to be delivered to the ventricles of patient 12. In fact, non-treatable rhythms may not be treated at all. In instances in which non-treatable rhythms are treated, however, stimulation module 74 does not deliver therapy to the ventricles of patient 12. Instead, stimulation module 74 may deliver therapy to other locations, including one or both atria.

Sometimes, a non-treatable arrhythmia (e.g., SVT) is conducted to the ventricles and falsely detected as VT or VF, resulting in the delivery of ventricular cardioversion, defibrillation or ATP therapy when no ventricular therapy is needed. Unnecessary delivery of ventricular therapy is generally uncomfortable for patient 12, needlessly depletes power source 80 and can sometimes induce more dangerous arrhythmias (e.g., actual VT or VF). It is desirable, therefore, to avoid delivering a ventricular stimulation therapy due to inappropriate detection of ventricular arrhythmias.

The techniques of this disclosure may increase the accuracy with which processor 70 detects arrhythmias and discriminates between treatable and non-treatable arrhythmias. Processor 70 may analyze rate characteristics over several cardiac event intervals to detect relative changes and/or variations over the most recent cardiac event intervals. To this end, processor 70 computes cardiac event intervals corresponding to the amount of time between sensed cardiac events (or beats). Processor 70 may, for example, compute NR-R intervals using the most recent N+1 sensed cardiac events. Although processor 70 is described as computing R-R intervals, other cardiac event intervals, such as P-P intervals corresponding to the amount of time between P-waves of consecutive beat or other type of cardiac intervals, may be used instead of or in addition to the R-R intervals.

Figure 4:
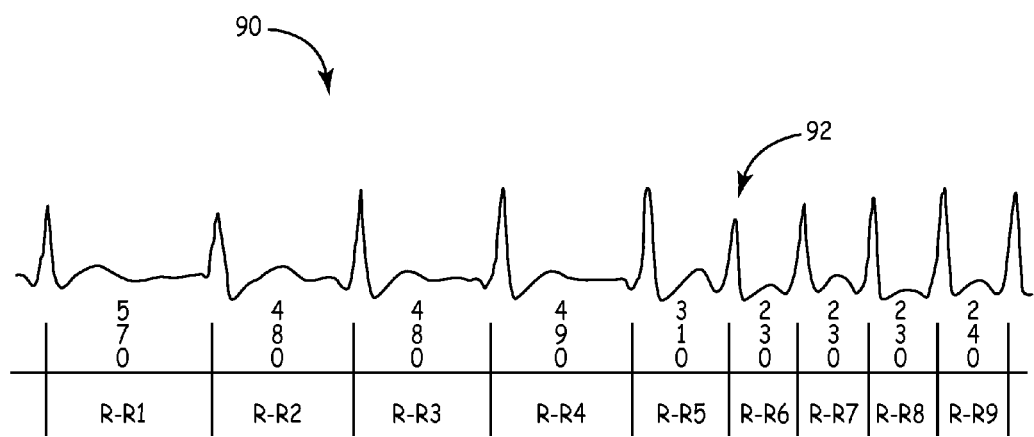
FIG. 4 is a timing diagram illustrating an electrogram (EGM) of a plurality of cardiac events.

In one instance, processor 70 may analyze the relative changes and/or variations over the last NR-R intervals to determine whether sudden rate onset is present. For purposes of description, processor 70 will be described as analyzing nine R-R intervals (i.e., N=9) constructed using the ten most recent beats (as shown in FIG. 4). However, processor 70 may analyze more or fewer cardiac event intervals in making the sudden rate onset determination.

Processor 70 calculates a relative change of the latest (i.e., the most recent) four R-R intervals (RCN4RR) with respect to previous intervals. In one example, processor 70 may calculate the relative change of the latest four R-R intervals as the difference between the sum of the oldest four R-R intervals of the nine R-R intervals and the sum of the most recent four R-R intervals of the nine R-R intervals divided by the sum of the most recent four R-R intervals (shown in equation 1 below). In another example, processor 70 may calculate the relative change as the difference between an average (e.g., mean, median or mode) of the oldest four R-R intervals of the nine R-R intervals and an average of the most recent four R-R intervals of the nine R-R intervals divided by the average of the most recent four R-R intervals (shown in equation 2 below). Processor 70 may use other techniques for determining a relative change of the most recent four R-R intervals with respect to previous intervals, such as the techniques described in U.S. Pat. No. 6,567,691 to Stadler, which is incorporated herein by reference in its entirety.

$$RCN4RR = \frac{\sum OLDEST\_RR - \sum LATEST\_RR}{\sum LATEST\_RR} \quad (1)$$

$$RCN4RR = \frac{AVG\_OLDEST\_RR - AVG\_LATEST\_RR}{AVG\_LATEST\_RR} \quad (2)$$

Processor 70 also calculates a variability (N4RRVar) of the most recent four R-R intervals of the nine R-R intervals. In one example, processor 70 calculates the variability as the difference between the maximum value of the latest four R-R intervals and the minimum of the latest four R-R intervals divided by the average of the latest four R-R intervals (shown in equation 3 below). Other techniques may be used to calculate the variability, such as computing a standard deviation of the most recent four R-R intervals.

$$N4RRVar = \frac{MAX\_LATEST\_RR - MIN\_LATEST\_RR}{AVG\_LATEST\_RR} \quad (3)$$

Processor 70 detects sudden rate onset when the calculated variability (N4RR Var) is less than a variability threshold value and the calculated relative change (RCN4RR) is greater than a relative change threshold value. In one example, the variability threshold value is equal to 33% of the average of the latest four R-R intervals and the relative change threshold value is equal to 50% of the sum of the latest four R-R intervals or the average of the latest four R-R intervals depending on whether the relative change is computed using equation (1) or (2), respectively. Other threshold values may be used, however. When processor 70 detects rate onset, processor 70 may set a rate onset flag associated with each ventricular event equal to one until rate offset is detected. Processor 70 may calculate the variability (N4RRVar) and relative change (RCN4RR) after every sensed ventricular event (which may include paced events) and analyze the calculated variability and relative change to monitor for sudden rate onset. Alternatively, processor 70 may calculate and analyze the variability and relative change at a different interval, e.g., after every other ventricular event, every third ventricular event or the like.

After detecting rate onset, processor 70 may monitor for rate offset. Rate offset occurs when the rate of ventricular events falls below a threshold. Processor 70 may monitor for rate offset by analyzing the rate of the last four R-R intervals of the nine R-R intervals. For example, processor 70 may compute an average of the latest (i.e., most recent) four R-R intervals and compare the average to a rate offset threshold. The rate offset threshold may, in some instances, be computed as a function of the average rate at the time of rate onset detection. Processor 70 may detect rate offset when the difference between the mean rate of the most recent four R-R intervals and the average heart rate at the time of rate onset detection is larger than the rate offset threshold. In one example, the rate offset threshold may be computed as 37.5% of the average rate at the time of rate onset. As such, when rate onset is detected, processor 70 may be configured to calculate the average heart rate at onset as the average of the most recent four R-R intervals and compute the rate offset threshold using the average heart rate at onset. In response to detecting rate offset, processor 70 sets the rate onset flag equal to 0.

Some non-treatable arrhythmias, such as certain types of SVTs, produce sudden rate onset characteristics that are similar to the sudden rate onset characteristics of treatable arrhythmias. As such, determining whether an arrhythmia is treatable or non-treatable based on sudden rate onset alone may result in false detection of a treatable arrhythmia. As such, processor 70 analyzes a morphology of an EGM associated with a ventricular event in response to detecting sudden rate onset. Doing so reduces the likelihood of false detections, thus providing a more reliable detection mechanism.

In accordance with the techniques of this disclosure, processor 70 identifies a location of the sudden rate onset initiation and analyzes a morphology of a beat subsequent to the location of the sudden rate onset initiation to distinguish between treatable and non-treatable arrhythmias. In one example, processor 70 analyzes the morphology of the first beat immediately subsequent to the location of the sudden onset initiation (i.e., the onset initiation beat). In the example described above in which nine R-R intervals are analyzed, the onset initiation beat is the sixth beat of the ten beats used to determine the nine R-R intervals as shown in FIG. 4. In this manner, the sudden rate onset detection is used to identify the beat on which processor 70 performs the morphology analysis. In other examples, processor 70 may analyze other beats subsequent to the sudden rate onset initiation, such as a second, third, fourth, fifth or sixth beat subsequent to the sudden rate onset. Therefore, although the techniques below are described as being performed on the onset initiation beat, similar techniques could be used on a different one of the beats located after the onset initiation. However, analyzing beats closer to the onset initiation may provide slightly better results since the successive beats may begin to stabilize. In any case, processor 70 may better discriminate treatable arrhythmias from non-treatable arrhythmias by performing morphology analysis on a single beat instead of using extensive processing resources to do morphology analysis on a plurality of beats.

Processor 70 analyzes the morphology of the onset initiation beat to determine whether the arrhythmia is treatable or non-treatable. Processor 70 may compare the EGM of the onset initiation beat to a template EGM to generate a matching metric. The template EGM may be an EGM of a beat during a known normal sinus rhythm, an EGM of a beat located prior to rate onset initiation or a beat located after the rate onset initiation. Processor 70 may compare the matching metric to a threshold to determine whether the morphology of the onset initiation beat is normal or abnormal compared to the template EGM. As described above, during VT or VF, the EGM of the onset initiation beat is typically different from an EGM of a beat during normal sinus rhythm or a beat during SVT. Additionally, two consecutive beats located after the rate onset initiation may also be substantially different in the case of VT or VF, but be the same during SVT. As such, the template beat may also be one of the beats located after rate onset initiation. Processor 70 may set a beat morphology flag equal to one when the beat is determined to be abnormal and set the beat morphology flag equal to zero when the beat is determined to be normal.

In one example, processor 70 may perform the morphology analysis using a wavelet transform of the sensed signal. One example technique for performing wavelet transforms on EGMs is described in U.S. Pat. No. 6,393,316 to Gillberg et al. ("the '316 patent"), which is incorporated herein by reference in its entirety. A wavelet transform is a mechanism for describing the evolution over time of signal frequency. The wavelet transform method performs "template matching," which is a mathematical comparison of a template EGM, e.g., of a ventricular event during normal sinus rhythm, to the EGM of the onset initiation beat to generate a matching metric. The matching metric in this case may be referred to as a wavelet matching score. The wavelet matching score generated by the template matching may take on a value between 0 and 100, with larger wavelet matching scores corresponding to a closer match between the EGM of the onset initiation beat and the template EGM. In one example, processor 70 determines that there is a match (i.e., the onset initiation beat is normal) when the wavelet matching score is greater than or equal to 70, and determines that there is not a match (i.e., the onset initiation beat is abnormal) when the wavelet matching score is less than 70. A normal beat is indicative of non-treatable arrhythmias and an abnormal beat is indicative of treatable arrhythmias. Alternatively, processor 70 may use other methods for comparing waveforms to generate the matching metric, including using an area of distance or a correlation waveform analysis metric, example techniques of which are also described in the '316 patent.

In another example, processor 70 performs the morphology analysis of the onset initiation beat by analyzing one or more beat morphology parameters instead of or in addition to the matching metric. The beat morphology parameters may include an R-wave symmetry index (RSI) that represents the ratio of onset-side slope to offset-side slope of the R-wave in the far-field EGM, R-wave width (RW) value that represents the width of the R-wave in the far-field EGM, Q-wave R-wave index (QRI) that represents the ratio of the Q-wave amplitude to the R-wave amplitude in the far-field EGM, R-wave polarity code (RPC) value that represents the R-wave polarities between the far-field EGM and the near-field EGM, and slope peak shift (SPS) that represents the time difference in slope peaks between the far-field EGM and the near-field EGM. Calculation of these beat morphology parameters will be described in more detail below. Other types of beat morphology parameters may also be used in addition to or instead of the beat morphology parameters listed above.

Processor 70 may calculate one or more beat morphology parameters for the EGM of the onset initiation beat and determine that the morphology is abnormal when one or more beat morphology parameters of the EGM have changed, e.g., are greater than or less than a respective threshold depending on the parameter. For example, processor 70 may compute a near-field matching metric, far-field matching metric, RSI, RW, QRI, RPC and SPS and determine that the morphology of the onset initiation beat is abnormal when the beat morphology parameters match a particular set of criteria. As one example, processor 70 may determine that the morphology of the onset initiation beat is abnormal when the beat morphology parameters are greater than or less than respective threshold values depending on the particular beat feature. Processor 70 may determine that the morphology of the onset initiation beat is abnormal when more or fewer of the calculated beat morphology parameters have changed.

In another example, the criteria may be more specific than a particular number of beat morphology parameters changing. For instance, the beat morphology of the onset initiation beat may be required to meet the criteria described below to be classified as treatable. If any of the rules of the criteria below is not met, processor 70 classifies the rhythm as non-treatable. The criteria below is especially effective if detecting premature ventricular contraction (PVC) initiated sudden rate onset. Other sets of criteria may be used for detecting PVC initiated sudden rate onset or other types of sudden rate onset not initiated by PVC.

Far-field EGM of current beat (i.e., most recent beat) is not corrupted by noise/artifacts; AND
Sudden rate onset is detected at current beat; AND
Current beat in gray zone between treatable and non-treatable (e.g., far-field wavelet matching score between 70 and 86); AND
The RPC of onset initiation beat changed relative to template; AND
The SPS of onset initiation beat changed at least 3 units relative to the template; AND
The max slope of the onset initiation beat is <=96 ADC counts (24 mV per second) in far-field EGM; AND
EITHER
(1)
The RW of onset initiation beat changed at least by 12 relative to the template; AND
The QRI of onset initiation beat changed at least by 2, relative to the template;
OR
(2)
The near-field EGM of the onset initiation beat is not corrupted by noise/artifacts; AND
The near-field WMS of onset initiation beat <=10; AND
The far-field WMS of onset initiation beat <=10.

In a further example, processor 70 may determine whether the morphology of the onset initiation beat is abnormal using a probability-correlation based model. One such model is described in copending U.S. patent application Ser. No. 12/415,445 to Zhang et al., which is incorporated herein by reference in its entirety. As described in detail in Zhang, processor 70 obtains a plurality of beat morphology parameters associated with the rhythm of heart 18. Processor 70 obtains probabilities that the rhythm is treatable based on each of the plurality of parameters separately. In other words, for each of the parameters, processor 70 determines the probability that the rhythm is treatable based on only the corresponding parameter. Additionally, processor 70 obtains correlations between each of the parameters and the other ones of the parameters. Processor 70 then determines whether the rhythm is treatable based on the determined probabilities and correlations. For example, processor 70 computes weights for each of the parameters based on the correlations. The weights represent the independent contribution coefficient to attribute to the respective parameters. Processor 70 computes an overall probability that the rhythm is treatable by weighting the probabilities by the corresponding independent contribution coefficient and summing the weighted probabilities.

As described above, the techniques may be used to analyze the morphology of an EGM associated with a beat other than the onset initiation beat. In any case, processor 70 need only perform morphology analysis on the EGM associated with a single beat to discriminate between a non-treatable arrhythmia with sudden onset and a treatable arrhythmia. This reduces the amount of processing resources used for morphology analysis, which is typically quite processing intensive, when compared to morphology techniques that discriminate based on morphologies of a plurality of ventricular events.

Processor 70 may utilize the rate onset flag and the beat morphology flag to determine whether the arrhythmia is treatable or non-treatable. When the rate onset flag and the beat morphology flag are equal to one, processor determines the arrhythmia is treatable, e.g., VT or VF. Processor 70 provides therapy in accordance with a therapy program for treatable arrhythmias. For example, processor 70 controls stimulation module 74 to deliver ventricular stimulation therapy, e.g., in the form of ATP, cardioversion shock(s), defibrillation shock (s) or a combination thereof. Processor 70 may further analyze the rhythm to further differentiate the type of treatable arrhythmia. For example, processor 70 may analyze the rate and regularity of the rhythm to determine whether the treatable rhythm is VT or VF. In the case of VT, stimulation module 74 may provide ATP and/or cardioversion may be delivered. In the case of VF, stimulation module 74 may deliver a defibrillation shock.

When either the rate onset flag or the beat morphology flag are not equal to one (i.e., one of them is equal to zero), processor determines the arrhythmia is non-treatable, e.g., SVT. Processor 70 controls stimulation module 74 to provide therapy in accordance with a therapy program for non-treatable arrhythmias. Processor 70 may control stimulation module 74 to not deliver electrical stimulation to the ventricles. Instead, processor 70 may control stimulation module 74 to deliver therapy to one or both atria or provide no therapy at all.

FIG. 4 is a timing diagram illustrating an EGM 90 of a plurality of cardiac events. In the example EGM of FIG. 4, the EGM includes ten ventricular cardiac events. As described above, processor 70 of IMD 14 analyzes the rate of cardiac events to detect sudden rate onset. Processor 70 may calculate cardiac event intervals corresponding to the amount of time between sensed cardiac events. In the example of FIG. 4, processor 70 calculates nine R-R intervals (labeled R-R1 through R-R9) using the ten most recent cardiac events. The values in milliseconds (ms) are shown above the respective intervals. In the example illustrated in FIG. 4, interval R-R1 is equal to 570 ms, interval R-R2 is equal to 480 ms, interval R-R3 is equal to 480 ms, interval R-R4 is equal to 490 ms, interval R-R5 is equal to 310 ms, interval R-R6 is equal to 230 ms, interval R-R7 is equal to 230 ms, interval R-R8 is equal to 230 ms, and interval R-R9 is equal to 240 ms. Interval R-R1 is the oldest R-R interval and R-R9 is the most recent R-R interval.

Processor 70 analyzes characteristics over the nine R-R intervals to detect whether sudden rate onset occurs. For example, processor 70 may analyze relative changes and/or variations over the last nine R-R intervals to determine whether sudden rate onset is present. As described above, processor 70 calculates a relative change of the most recent four R-R intervals, i.e., intervals R-R6 through R-R9 in FIG. 4, with respect to previous intervals. Processor 70 may calculate the relative change of the most recent four R-R intervals as the difference between the sum of the oldest four R-R intervals, i.e., intervals R-R1 through R-R4 in FIG. 4, and the sum of the most recent four R-R intervals divided by the sum of the most recent four R-R intervals (shown in equation 1 above). Alternatively, processor 70 may calculate the relative change as the difference between an average of the oldest four R-R intervals and an average of the most recent four R-R intervals divided by the average of the most recent four R-R intervals (shown in equation 2 above). Processor 70 may calculate the relative change using other techniques, including using more or fewer R-R intervals.

Processor 70 may also calculate a variability over the most recent four R-R intervals, i.e., intervals R-R6 through R-R9 in FIG. 4. For example, processor 70 may calculate the variability as the difference between the maximum value of the latest four R-R intervals (240 ms in the example of FIG. 4) and the minimum value of the latest four R-R intervals (230 ms in the example of FIG. 4) divided by the average of the latest four R-R intervals (shown in equation 3 above). Other techniques may be used to calculate the variability, such as computing a standard deviation of the most recent four R-R intervals.

Processor 70 detects sudden rate onset when the calculated variability is less than a variability threshold value and the calculated relative change is greater than a relative change threshold value. As described above, some non-treatable arrhythmias, such as certain types of SVTs, produce rate onset characteristics that are similar to rate onset characteristics of treatable arrhythmias. As such, determining whether an arrhythmia is treatable or non-treatable based on sudden rate onset alone may result in false detection of a treatable arrhythmia.

Therefore, processor 70 identifies a location at which initiation of the sudden rate onset occurs. In the example of FIG. 4, sudden rate onset is initiated at the location to which arrow 92 points. As described in detail above, processor 70 analyzes a morphology of an EGM associated with a beat located after the rate onset initiation (at arrow 92) to distinguish between treatable and non-treatable arrhythmias. In one example, processor 70 may analyze the morphology of an EGM associated with the first beat after the onset initiation. As can be seen in FIG. 4, the onset initiation beat may be the first ventricular event of the events that occur at the faster rate, i.e., the sixth ventricular event in the example illustrated.

Processor 70 analyzes the morphology of the identified beat as described in detail above. For example, processor 70 may analyze the morphology of the identified initiation beat by determining one or more parameters associated with the identified beat and comparing it to parameters associated with a beat during a normal sinus rhythm. Processor 70 may compute the parameters using any of the techniques described above. In this manner, processor 70 uses the rate onset detection to identify the beat on which to perform the morphology analysis. Doing so enables processor 70 to better discriminate treatable arrhythmias from non-treatable arrhythmias, thus providing a more reliable detection mechanism. Moreover, processor 70 reduces the processing intensive tasks by identifying a single ventricular event for which the morphology analysis is to be performed.

Although FIG. 4 is described in regards to analyzing R-R intervals, other cardiac event intervals may be used, such as P-P intervals corresponding to the amount of time between P-waves of consecutive beat, or a combination of different types of cardiac intervals. Additionally, processor 70 may analyze more or fewer than nine cardiac event intervals in making the rate onset determination. Furthermore, processor 70 may analyze the morphology of a different ventricular event, such as a second, third, fourth, fifth or sixth ventricular event after the location at which the rate onset is determined to occur.

Figure 5:
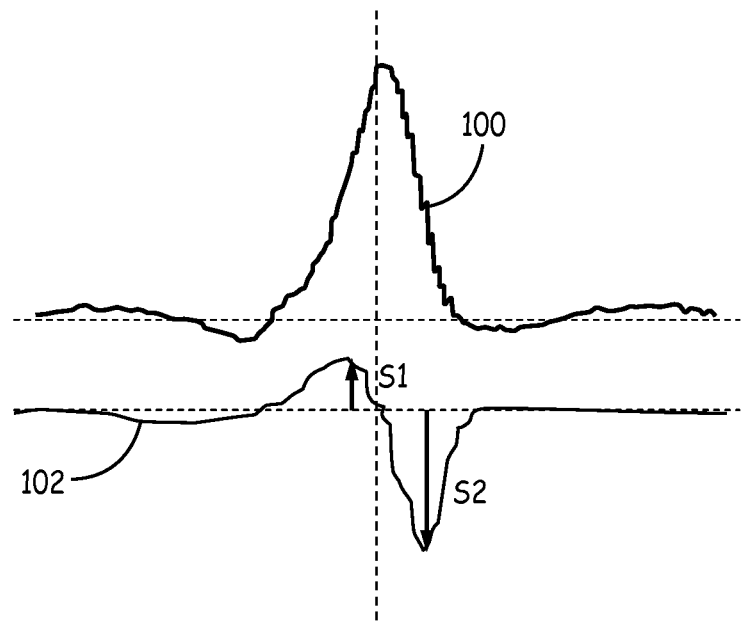
FIGS. 5-9 are timing diagrams illustrating example EGMs over a period of time and techniques for computing various beat morphology parameters using the EGMs.

FIGS. 5-9 are timing diagrams illustrating example portions of EGMs over a period of time and techniques for computing various beat morphology parameters using the EGMs. FIG. 5 is timing diagram illustrating an example portion of a far-field EGM signal 100 of a heart beat and a technique to compute the RSI of far-field EGM signal 100. Below the far-field EGM signal 100 is a curve 102 that represents the slope of far-field EGM signal 100. Processor 70 of IMD 14 computes a peak value of the onset-side slope (labeled S1 in FIG. 5) and a peak value of the offset-side slope (labeled S2 in FIG. 5). The RSI is computed as the absolute value of the ratio of the peak value of the onset-side slope to the peak value of the offset-side slope of the far-field EGM multiplied by the factor of 10. Multiplying by the factor of 10 converts the RSI value to resolution 10. In other examples, other resolutions may be used.

Figure 6:
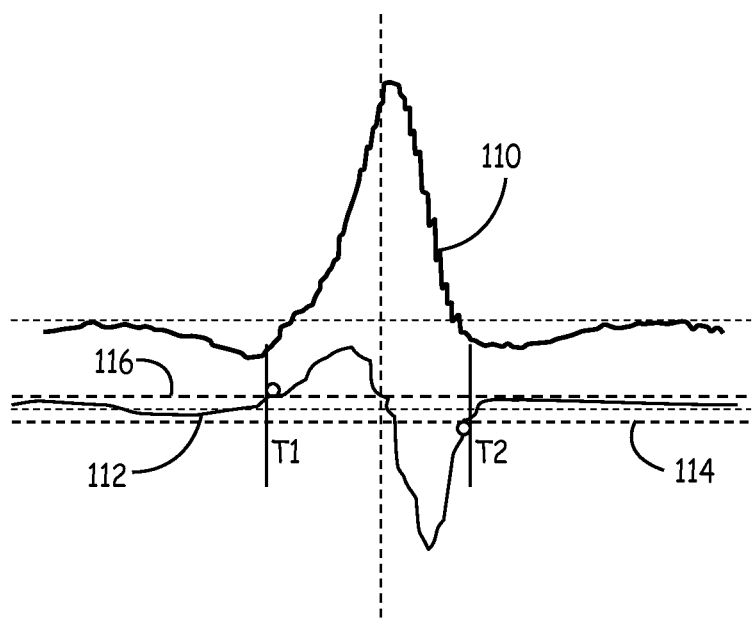

FIG. 6 is a timing diagram illustrating another example portion of a far-field EGM signal 110 and a technique for computing the RW of far-field EGM signal 110. Below the far-field EGM signal 110 is a curve 112 that represents the slope of far-field EGM signal 110. Processor 70 of IMD 14 computes overall maximum absolute slope peak value, referred to herein as Max_Slope, from the portion of the EGM. RW is equal to the time (labeled T2 in FIG. 6) at which the offset slope is equal to ⅛ of the Max_Slope (represented by dashed line 114) minus the time (labeled T I in FIG. 6) at which the onset slope is equal to ⅛ of the Max_Slope (represented by dashed line 116).

Figure 7:
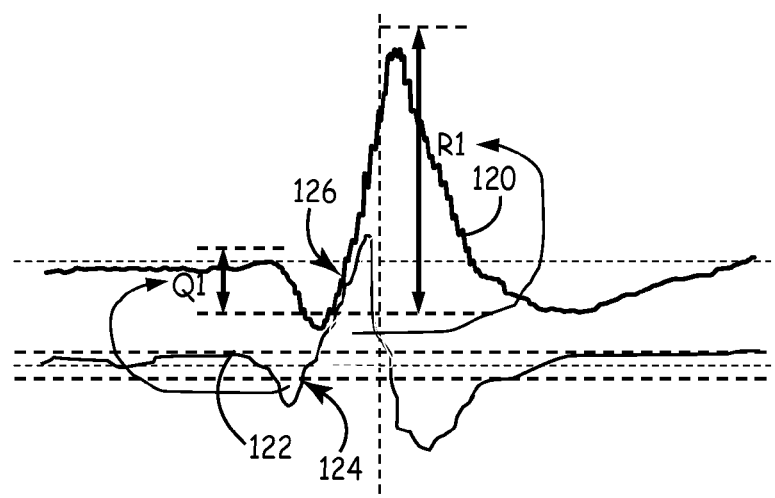

FIG. 7 is a timing diagram illustrating another example portion of a far-field EGM signal 120 and a technique for computing the QRI of far-field EGM signal 120. Below the far-field EGM signal 120 is a curve 122 that represents the slope of far-field EGM signal 120. Processor 70 of IMD 14 computes a peak amplitude of a Q-wave of far-field EGM signal 120 (labeled Q1 in FIG. 7) and a peak amplitude of an R-wave of far-field EGM signal 120 (labeled R1 in FIG. 7). The QRI is computed as the absolute value of the ratio of the peak amplitude of a Q-wave to the peak amplitude of an R-wave of the far-field EGM multiplied by the factor of 10. This ratio may be obtained by computing the ratio of the integration of the amplitude of the left side lobe pulse 124 of the slope signal to the integration of the amplitude of the main pulse 126 of the slope signal multiplied by 10. Multiplying by the factor of 10 converts the QRI value to resolution 10. In other examples, other resolutions may be used.

Figure 8:
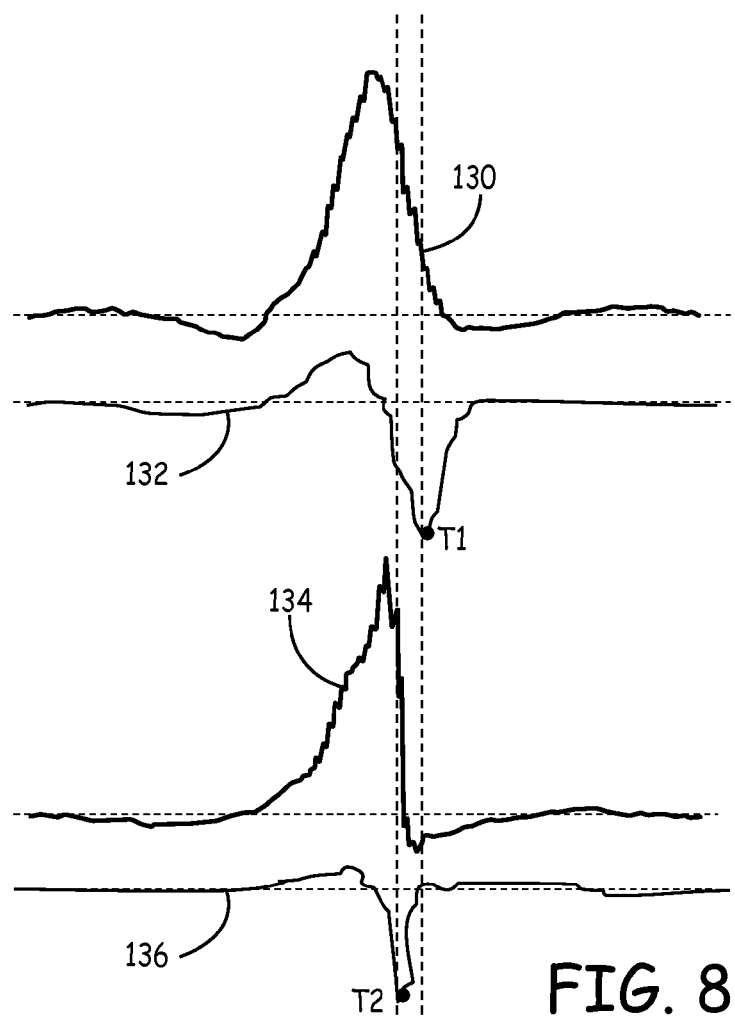

FIG. 8 is a timing diagram illustrating an example portion of a far-field EGM signal 130 and a near-field EGM signal 134. Below each of the EGM signals 130 and 134 are curves 132 and 136 that represent the slopes of far-field EGM signal 130 and near-field EGM signal 134, respectively. Processor 70 of IMD 14 computes a time at which the slope of far-field EGM signal 130 has a peak amplitude (labeled T1 in FIG. 8) and a time at which the slope of near-field EGM signal 134 has a peak amplitude (labeled T2 in FIG. 8). Processor 70 computes SPS as the difference between T1 and T2 (i.e., T1-T2).

Figure 9:
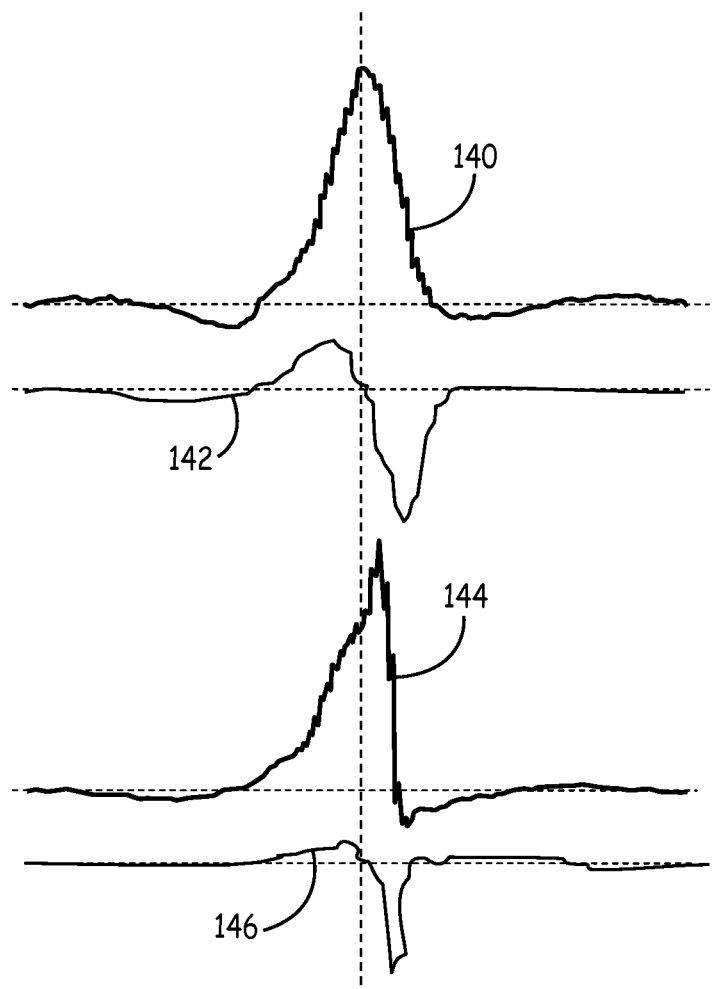

FIG. 9 is a timing diagram illustrating example portion of a far-field EGM signal 140 and a near-field EGM signal 144. Below each of the EGM signals 140 and 144 are curves 142 and 146, respectively, that represent the slopes of far-field EGM signal 140 and near-field EGM signal 144. Processor 70 of IMD 14 determines a polarity (i.e., +or −) of far-field EGM signal 140 and a polarity (i.e., +or −) of near-field EGM signal 144. Processor 70 may determine the polarity of the R-wave of the near-field and far-field EGMs using the main pulse and either the left side lobe pulse or right side lobe pulse. In particular, processor 70 may identify a positive polarity of the EGM signal when a peak-valley pattern is identified in the slope signal and identify a negative R-wave polarity of the EGM signal when a valley-peak pattern is identified in the slope signal. The RPC is the combination of polarity of the far-field EGM signal and the polarity of the near-field EGM, and takes on one of four values; ++, +−, −+or −−. Among beats with changed RPC relative to the template, approximately 89% are VT/VF beats and among beats without changed RPC relative to the template, approximately 36% are VT/VF beats.

Processor 70 of IMD 14 may calculate the beat morphology parameters as described in detail below. Other techniques for calculating the beat morphology parameters may be used, however. As such, the description below is only one example way in which the morphology parameters may be computed. Initially, processor 70 obtains a portion of a far-field EGM around a beat of interest. The portion of the EGM may, for example, include forty-eight data points centered at a ventricular sense marker of the beat of interest. Processor 70 initially obtains a slope (first order derivative) of the input data in the window, and if the max slope (MaxSlope)≥96 ADC units (e.g., 24 mV per second) processor 70 continues to calculate beat morphology parameters. If MaxSlope<96, feature LowSlope is detected and no further calculation is performed.

Processor 70 searches for any possible positive or negative pulse in the slope signal, no matter how big or small, wide or narrow the pulse is. For each pulse in the slope signal, processor 70 calculates the characteristics of the pulse, including polarity, peak position (i.e., the data point in the window with max absolute amplitude), peak value (i.e., max absolute value in ADC counts), width (in data points), start point, end point, and "mergeable flag." If a pulse has a width <3 data points and peak value <224 ADC counts (218.75 uV), then the mergeable flag is set.

Processor 70 identifies all of the pulses in the slope signal with peak values larger than one-eighth of the MaxSlope and that are not mergeable (as indicated by the mergeable flag) and labels these pulses as large pulses. Processor 70 then starts merging the instantly neighboring large pulses, which are side by side to each other with the same polarity and not separated by any other large pulse with opposite polarity. After the merging, the characteristics of the merged pulse are updated accordingly.

Processor 70 then searches for the main pulse of the slope signal, which is the merged pulse with the largest peak value. Processor 70 may also search for any possible nearest left side lobe pulse and right side lobe pulse with opposite polarity to the main pulse. Processor 70 determines the polarity of the R-wave using the main pulse and either the left side lobe pulse or right side lobe pulse. In particular, processor 70 may identify a positive R-wave polarity of the EGM signal when a peak-valley pattern is identified in the slope signal and identify a negative R-wave polarity of the EGM signal when a valley-peak pattern is identified in the slope signal.

Processor 70 calculates the QRI (in resolution 10) as the ratio of the integration of the amplitude of the left side lobe pulse of the slope signal to the integration of the amplitude of the main pulse of the slope signal multiplied by 10. Processor 70 computes the RSI (in resolution 10) as the ratio of the peak values of the two paired slope pulses multiplied by ten. Processor 70 also calculates the RW (in data points), SPS (in data points) from the corresponding FF and NF beats, and also RPC ("1" means both far-field and near-field R-waves have positive polarity, "2" means far-field R-wave has positive polarity and near-field R-wave has negative polarity, "3" means far-field R-wave has negative polarity and near-field R-wave has positive polarity, and "4" means both far-field and near-field R-waves have negative polarity).

Processor 70 may perform a similar analysis of a portion of a template EGM to obtain beat morphology parameters for a template beat to which the beat morphology parameters of the beat of interest are compared. The beat morphology parameters of the template beat may be stored within memory 78 for later retrieval and comparison by processor 70. As described above, the techniques for computing the beat morphology parameters described above are just one technique for determining the values of the beat morphology parameters. Other techniques may be used to compute these various beat morphology parameters and/or other beat morphology parameters.

Figure 10:
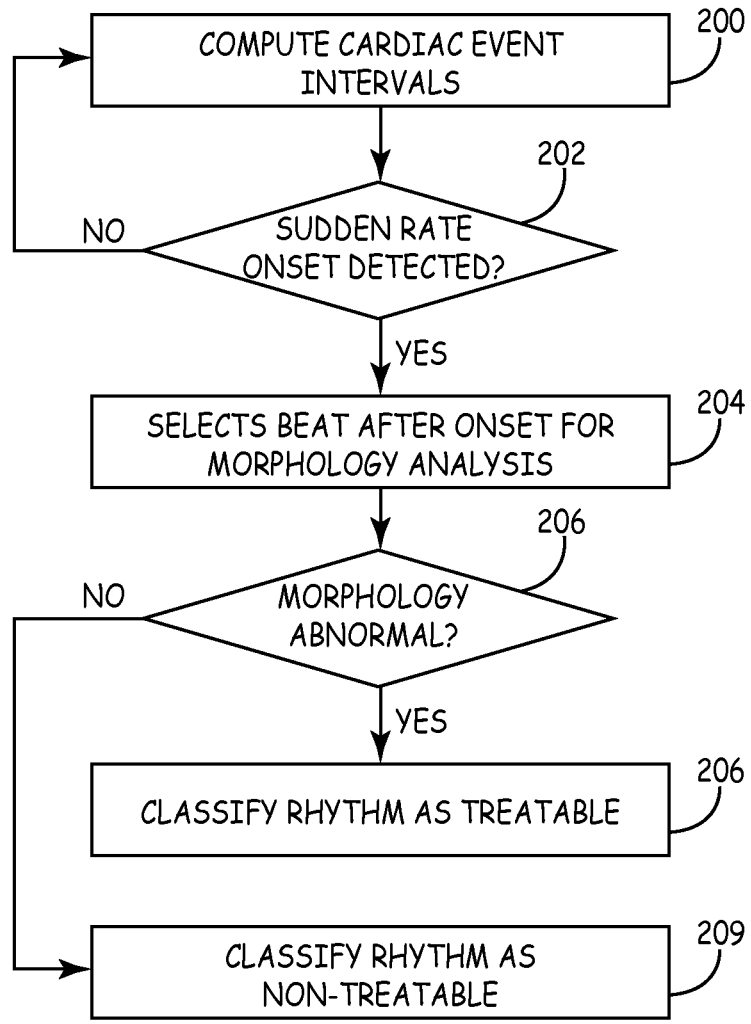
FIG. 10 is a flow diagram illustrating example operation of an IMD performing the arrhythmia detection techniques of this disclosure.

FIG. 10 is a flow diagram illustrating example operation of an IMD, such as IMD 14, performing the arrhythmia detection techniques of this disclosure. Processor 70 may calculate a plurality of cardiac event intervals corresponding to the amount of time between sensed cardiac events (200). Processor 70 may compute Ncardiac event intervals using the N+1 most recent sensed cardiac events.

Processor 70 analyzes characteristics over the computed cardiac event intervals to determine whether sudden rate onset is initiated (202). Processor 70 may, for example, calculate a variability among a first portion of the plurality of cardiac event intervals, e.g., of the most recent four cardiac event intervals of the nine cardiac event intervals. Processor 70 may calculate the variability using equation (3) above. Processor 70 may also calculate a relative change of the first portion of the plurality of cardiac event intervals with respect to a second portion of the cardiac event intervals, e.g., in accordance with equations (1) or (2) above. Processor 70 detects sudden rate onset when the calculated variability is less than a variability threshold value and the calculated relative change is greater than a relative change threshold value.

When processor 70 does not detect sudden rate onset ("NO" branch of 202), processor 70 computes a subsequent cardiac event interval. When processor 70 detects sudden rate onset ("YES" branch of 202), processor 70 selects a cardiac event after onset initiation for morphology analysis (204). In one example, processor 70 selects the first beat immediately subsequent to the location of the sudden onset initiation, referred to as the onset initiation beat. In other examples, processor 70 may analyze other beats subsequent to the sudden rate onset initiation, such as a second, third, fourth, fifth or sixth beat subsequent to the sudden rate onset.

Processor 70 determines whether the morphology of the selected cardiac event is abnormal (206). Processor 70 may compute one or more morphology parameters of the EGM associated with the selected cardiac event and compare the morphology parameters to respective morphology parameters of a template EGM to determine whether the cardiac event is normal or abnormal. Processor 70 may determine the cardiac event is abnormal when one or more morphology parameters (or a particular subset of those parameters) have changed by threshold amounts compared to the respective morphology parameters of the template EGM.

When processor 70 determines the morphology of the selected beat is abnormal ("YES" branch of 206), processor 70 classifies the rhythm as treatable (208). When processor 70 determines the morphology of the selected beat is not abnormal ("NO" branch of 206), processor 70 classifies the rhythm as non-treatable (209). Processor 70 may control stimulation module 74 to provide therapy based on the type of rhythm (i.e., treatable or non-treatable) that is detected.

Figure 11:
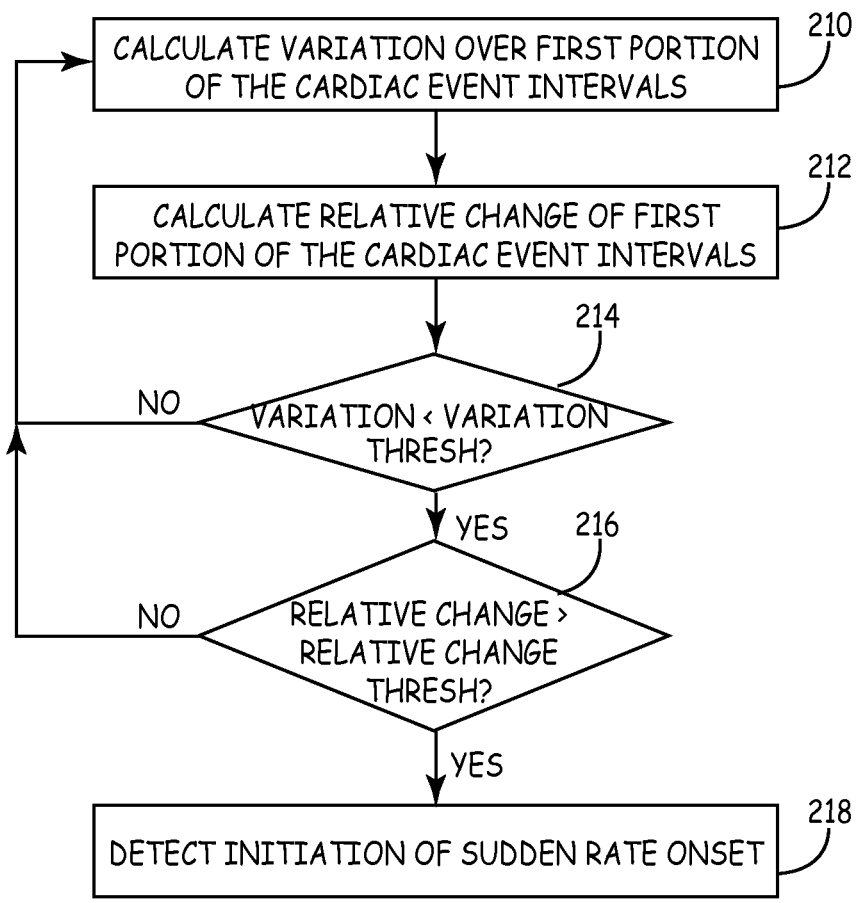
FIG. 11 is a flow diagram illustrating example operation of an IMD detecting initiation of sudden rate onset by analyzing characteristics over a plurality of computed cardiac event intervals.

FIG. 11 is a flow diagram illustrating example operation of an IMD, such as IMD 14, detecting initiation of sudden rate onset by analyzing characteristics over a plurality of computed cardiac event intervals. For purposes of description, processor 70 of IMD 14 will be described as analyzing the characteristics over nine computed cardiac events. However, the plurality of cardiac event intervals may include more or fewer cardiac event intervals.

Processor 70 calculates a variation over a first portion of the cardiac event intervals (210). As an example, processor 70 may calculate the variation over the four most recent cardiac event intervals of the nine cardiac event intervals. Processor 70 also calculates a relative change of the first portion of the cardiac event intervals with respect to a second portion of the cardiac event intervals (212). For example, processor 70 may calculate a relative change of the four most recent cardiac event intervals with respect to the four oldest cardiac event intervals of the nine cardiac event intervals.

Processor 70 determines whether the calculated variation is less than a threshold variation value (214). When the variation is not less than the threshold variation value ("NO" branch of 214), processor 70 calculates the variation for a new set of cardiac event intervals that includes a subsequent cardiac event interval. When the variation is less than the threshold variation value ("YES" branch of 214), processor 70 determines whether the relative change of the first portion of the cardiac event intervals is greater than a threshold relative change value (216).

When the relative change is not greater than the threshold relative change value ("NO" branch of 216), processor 70 calculates the variation for a new set of cardiac event intervals that includes a subsequent cardiac event interval. When the relative change is greater than the threshold relative change value ("YES" branch of 216), processor 70 detects initiation of sudden rate onset (218).

Figure 12:
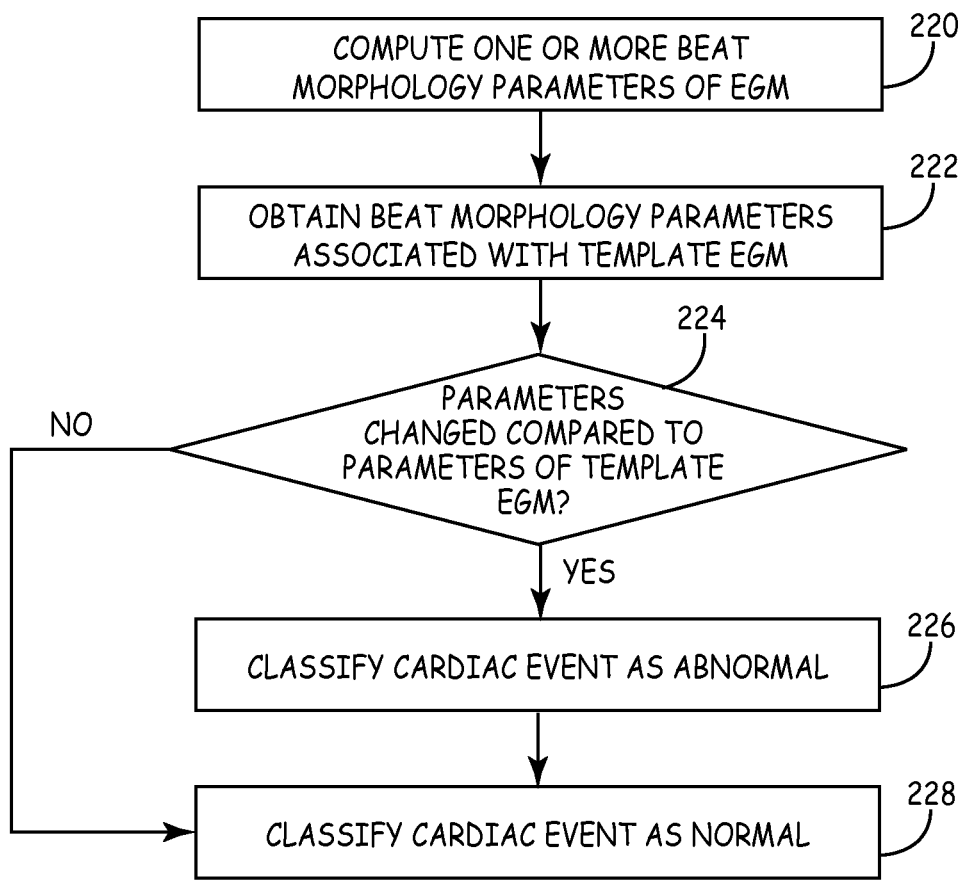
FIG. 12 is a flow diagram illustrating example operation of an IMD analyzing a morphology of a selected cardiac event subsequent to the location of the rate onset initiation.

FIG. 12 is a flow diagram illustrating example operation of an IMD, such as IMD 14, analyzing a morphology of a selected cardiac event subsequent to the location of the rate onset initiation. Processor 70 of IMD 14 computes one or more beat morphology parameters of an EGM associated with the selected cardiac event (220). Processor 70 of IMD 14 obtains corresponding beat morphology parameters of a template EGM (222). The template EGM may be an EGM of a cardiac event during normal sinus rhythm, an EGM of a cardiac event just prior to rate onset initiation, or another cardiac event after the rate onset initiation. The beat morphology parameters of the template EGM may be pre-computed and stored within memory 78.

Processor 70 determines whether one or more beat morphology parameters (or a particular subset of those parameters) of the EGM associated with the selected cardiac event have changed compared to the respective parameters of the template EGM (224). When the one or more beat morphology parameters (or a particular subset of those parameters) of the EGM associated with the selected cardiac event have changed compared to the respective parameters of the template EGM, processor 70 classifies the cardiac event as abnormal (226). When the one or more beat morphology parameters (or a particular subset of those parameters) of the EGM associated with the selected cardiac event have not changed compared to the respective parameters of the template EGM, processor 70 classifies the cardiac event as normal (228).

The techniques described in this disclosure, including those attributed to IMD 14 or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete digital, analog or logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. However, these examples should not be considered limiting of the techniques as described herein. Although this disclosure is mainly described in the context of detecting whether an arrhythmia is shockable or non-shockable, the techniques of this disclosure may be used to integrate multiple parameters together to determine whether other conditions of a patient exist based on determined probabilities associated with the parameters and correlations between each of the parameters. For example, such techniques may be used for heart failure monitoring, cardiac ischemia detection, discriminating extra-cardiac noise from true cardiac signals, epilepsy monitoring and control, non-invasive risk stratification, medical diagnostic testing, patient wellness monitoring, or in other cardiac or non-cardiac contexts. These and other examples are within the scope of the following claims.

The invention claimed is:

1. An implantable medical device (IMD) comprising:
a sensing module configured to acquire signals associated with a plurality of cardiac events cardiac events of a heart of a patient via at least one sensor; and
a processor configured to compute a plurality of cardiac event intervals, wherein each of the cardiac event intervals corresponds to an amount of time between successive ones of the plurality of cardiac events, detect rate onset of a rhythm of the heart of the patient based at least on one of relative changes and variations over the plurality of cardiac event intervals, identify a location of the initiation of rate onset among the plurality of cardiac events used to compute the plurality of cardiac event intervals used for detection of the rate onset, obtain an electrogram (EGM) of one of the cardiac events of the plurality of cardiac events used to compute the plurality of cardiac event intervals used for detection of the rate onset and located subsequent to the after a location of the initiation of the rate onset, analyze a morphology of the obtained EGM associated with the cardiac event after the location of the initiation of the rate onset, and determine whether the rhythm is indicative of a treatable rhythm based on the analysis of the morphology of the obtained EGM.

2. The device of claim 1, wherein the processor is configured to obtain an EGM of a first cardiac event after the location of the initiation of the rate onset.

3. The device of claim 1, wherein the processor is configured to analyze characteristics over the plurality of cardiac event intervals to detect the initiation of the rate onset of the rhythm by:
determining a variability among a first portion of the plurality of cardiac event intervals;
determining a relative change of the first portion of the plurality of cardiac event intervals with respect to a second portion of the plurality of cardiac event intervals, wherein the first portion of the plurality of cardiac event intervals occurred more recently in time than the second portion of the plurality of cardiac event intervals; and
detecting rate onset when the computed variability is less than a variability threshold value and the computed relative change is greater than a relative change threshold value.

4. The device of claim 3, wherein the processor is configured to obtain an EGM of an oldest cardiac event of the first portion of the cardiac event intervals.

5. The device of claim 3, wherein the processor is configured to monitor for rate offset after detecting the rate onset.

6. The device of claim 3, wherein the plurality of cardiac event intervals are R-R intervals corresponding to amount of time between successive R-waves.

7. The device of claim 1, wherein the processor is configured to:
compute one or more morphology parameters of the EGM of the cardiac event after the location of the initiation of the rate onset;
determine the rhythm is indicative of a treatable rhythm when the one or more morphology parameters have changed by threshold amounts compared to respective morphology parameters of a template EGM, and
determine the rhythm is indicative of a non-treatable rhythm when the one or more morphology parameters have not changed by threshold amounts compared to respective morphology parameters of the template EGM.

8. The device of claim 7, wherein the treatable rhythm comprises one of a ventricular tachycardia (VT) or a ventricular fibrillation (VF) and the non-treatable rhythm comprises a supra-ventricular tachycardia (SVT).

9. The device of claim 7, wherein the template EGM comprises one of an EGM of a cardiac event during normal sinus rhythm, an EGM of a cardiac event just prior to the initiation of the rate onset, or an EGM of another cardiac event after the initiation of the rate onset.

10. The device claim 7, wherein the one or more morphology parameters associated with the EGM include one or more of a matching metric, an R-wave symmetry index (RSI), a R-wave width (RW), a Q-R index (QRI), a R-wave polarity code (RPC) and a slope peak shift (SPS).

11. A method comprising:
    acquiring, via at least one sensor, signals associated with a plurality of cardiac events of a heart of a patient;
    computing, with a processor, a plurality of cardiac event intervals, wherein each of the cardiac event intervals corresponds to an amount of time between successive ones of the plurality of cardiac events;
    detecting, with the processor, rate onset of a rhythm of the heart of the patient based at least on one of relative changes and variations over the plurality of cardiac event intervals;
    identifying, with the processor, a location of the initiation of rate onset among the plurality of cardiac events used to compute the plurality of cardiac event intervals used for detection of the rate onset;
    obtaining, with the processor, an electrogram (EGM) of one of the cardiac events of the plurality of cardiac events used to compute the plurality of cardiac event intervals used for detection of the rate onset and located subsequent to the location of the initiation of the rate onset;
    analyzing, with the processor, a morphology of the obtained EGM; and
    determining, with the processor, whether the rhythm is indicative of a treatable rhythm based on the analysis of the morphology of the obtained EGM.

12. The method of claim 11, wherein obtaining the EGM of one of the cardiac events comprises obtaining an EGM of a first one of the cardiac events of the plurality of cardiac event located subsequent to the location of the initiation of the rate onset.

13. The method of claim 11, wherein analyzing, with the processor, characteristics over the plurality of cardiac event intervals to detect rate onset of the rhythm comprises:
    determining a variability among a first portion of the plurality of cardiac event intervals;
    determining a relative change of the first portion of the plurality of cardiac event intervals with respect to a second portion of the plurality of cardiac event intervals, wherein the first portion of the plurality of cardiac event intervals occurred more recently in time than the second portion of the plurality of cardiac event intervals; and
    detecting rate onset when the computed variability is less than a variability threshold value and the computed relative change is greater than a relative change threshold value.

14. The method of claim 13, wherein obtaining the EGM of the one of the plurality of cardiac events comprises obtaining an EGM of an oldest cardiac event used in determining the first portion of the cardiac event intervals.

15. The method of claim 13, further comprising monitoring for rate offset after detecting the rate onset.

16. The method of claim 11, wherein the plurality of cardiac event intervals are R-R intervals corresponding to amount of time between successive R-waves.

17. The method of claim 11, wherein analyzing the morphology of the EGM comprises computing one or more morphology parameters of the EGM of the cardiac event after the location of the initiation of the rate onset; and
    determining whether the rhythm is indicative of a treatable rhythm comprises:
        determining the rhythm is indicative of a treatable rhythm when the one or more morphology parameters have changed by threshold amounts compared to respective morphology parameters of a template EGM, and
        determining the rhythm is indicative of a non-treatable rhythm when the one or more morphology parameters have not changed by threshold amounts compared to respective morphology parameters of the template EGM.

18. The method of claim 17, wherein:
    determining that the rhythm is treatable comprises determining that the rhythm is indicative of one of a ventricular tachycardia (VT) or a ventricular fibrillation (VF); and
    determining that the rhythm is non-treatable comprises determining that the rhythm is indicative of a supraventricular tachycardia (SVT).

19. The method of claim 17, wherein the template EGM comprises one of an EGM of a cardiac event during normal sinus rhythm, an EGM of a cardiac event just prior to the initiation of the rate onset, or an EGM of another cardiac event after the initiation of the rate onset.

20. The method claim 17, wherein the one or more morphology parameters associated with the EGM include one or more of a matching metric, an R-wave symmetry index (RSI), a R-wave width (RW), a Q-R index (QRI), a R-wave polarity code (RPC) and a slope peak shift (SPS).

21. A computer-readable storage medium comprising instructions that, when executed by a processor in an implantable medical device, cause the processor to:
    acquire signals associated with a plurality of cardiac events of a heart of a patient;
    compute a plurality of cardiac event intervals, wherein each of the cardiac event intervals corresponds to an amount of time between successive ones of the plurality of cardiac events;
    detect rate onset of a rhythm of the heart of the patient based at least on one of relative changes and variations over the plurality of cardiac event intervals;
    identify a location of the initiation of rate onset among the plurality of cardiac events used to compute the plurality of cardiac event intervals used for detection of the rate onset;
    obtain an electrogram (EGM) of one of the cardiac events of the plurality of cardiac events used to compute the plurality of cardiac event intervals used for detection of the rate onset and located subsequent to the location of the initiation of the rate onset;
    analyze a morphology of the EGM associated with the cardiac event after the location of the initiation of the rate onset; and
    determine whether the rhythm is indicative of a treatable rhythm based on the analysis of the morphology of the EGM.

22. The computer-readable storage medium of claim 21, wherein instructions to obtain the EGM of one of the cardiac events comprises obtaining an EGM of a first one of the cardiac events of the plurality of cardiac event located subsequent to the location of the initiation of the rate onset.

23. The computer-readable storage medium of claim 21, wherein instructions to analyze characteristics over the plurality of cardiac event intervals to detect the rate onset of the rhythm comprise instructions that, when executed, cause the processor to:
    determine a variability among a first portion of the plurality of cardiac event intervals;
    determine a relative change of the first portion of the plurality of cardiac event intervals with respect to a second portion of the plurality of cardiac event intervals, wherein the first portion of the plurality of cardiac event intervals occurred more recently in time than the second portion of the plurality of cardiac event intervals; and detect rate onset when the computed variability is less than a variability threshold value and the computed relative change is greater than a relative change threshold value.

24. The computer-readable storage medium of claim 23, wherein instructions to obtain the EGM of the cardiac event comprise instructions to obtain an EGM of an oldest cardiac event used in determining the first portion of the cardiac event intervals.

25. The computer-readable storage medium of claim 21, wherein instructions analyze the morphology of the EGM comprise instructions to compute one or more morphology parameters of the EGM of the cardiac event after the location of the initiation of the rate onset; and instructions to determine whether the rhythm is indicative of a treatable rhythm comprise instructions to:

determine the rhythm is indicative of a treatable rhythm when the one or more morphology parameters have changed by threshold amounts compared to respective morphology parameters of a template EGM, and determine the rhythm is indicative of a non-treatable rhythm when the one or more morphology parameters have not changed by threshold amounts compared to respective morphology parameters of the template EGM.

\* \* \* \* \*